United States Patent
Brizzolara

(12)
(10) Patent No.: US 6,235,541 B1
(45) Date of Patent: May 22, 2001

(54) PATTERNING ANTIBODIES ON A SURFACE

(75) Inventor: Robert A. Brizzolara, Beltsville, MD (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 09/306,386

(22) Filed: May 6, 1999

Related U.S. Application Data

(60) Division of application No. 09/145,993, filed on Sep. 3, 1998, now abandoned, which is a continuation-in-part of application No. 08/816,337, filed on Mar. 13, 1997, now Pat. No. 5,858,801.

(51) Int. Cl.[7] .................................................. G01N 33/533
(52) U.S. Cl. .......................... 436/518; 430/302; 430/304; 430/298; 430/297; 430/299; 422/57; 422/60; 435/33; 435/287.8; 435/287.9; 435/973; 436/527; 427/2.11; 427/2.13; 427/466; 427/470; 427/504; 427/534; 427/288; 427/286
(58) Field of Search .................................... 430/302, 304, 430/298, 297, 299; 422/57, 60; 435/33, 287.8, 287.9, 973; 436/518, 527; 427/2.11, 2.13, 466, 470, 504, 534, 288, 286

(56) References Cited

U.S. PATENT DOCUMENTS

| | | |
|---|---|---|
| 3,941,876 | 3/1976 | Marinkovich . |
| 3,960,490 | 6/1976 | Giaever . |
| 4,011,308 | 3/1977 | Giaever . |
| 4,011,350 | 3/1977 | Markovits et al. . |
| 4,092,116 | 5/1978 | Giaever . |
| 4,157,895 | 6/1979 | Finlay et al. . |
| 4,259,433 | 3/1981 | Mizobuchi et al. . |
| 4,262,186 | 4/1981 | Provancher . |
| 4,417,948 | 11/1983 | Mayne-Banton et al. . |
| 4,591,570 | 5/1986 | Chang . |
| 4,764,485 | 8/1988 | Loughran et al. . |
| 4,826,755 | 5/1989 | Garbassi et al. . |
| 5,391,463 | 2/1995 | Ligler et al. . |
| 5,512,492 | 4/1996 | Herron et al. . |
| 5,516,703 | 5/1996 | Caldwell et al. . |
| 5,643,472 | 7/1997 | Engelsberg et al. . |
| 5,858,801 | 1/1999 | Brizzolara . |

*Primary Examiner*—Christopher L. Chin
*Assistant Examiner*—Bao-Thuy L. Nguyen
(74) *Attorney, Agent, or Firm*—John Forrest; Jacob Shuster

(57) ABSTRACT

Substrates are patterned with antibodies attached thereto at discrete locations from which absorption resistant coating is removed by selectively controlled mechanical scribing contact to avoid chemical removal so as to decrease fabrication costs and increase fabrication speed.

5 Claims, 2 Drawing Sheets

PATTERNING ANTIBODIES ON A SURFACE

The present invention relates in general to patterning techniques utilized in the fabrication of devices such as multi-analyte biosensors utilized for environmental monitoring and medical diagnostic purposes as disclosed in U.S. application Ser. No. 09/145,993, filed Sep. 3, 1998, now abandon, as a division of parent application Ser. No. 08/816,337, filed Mar. 13, 1997, now U.S. Pat. No. 5,858,801 issued Jan. 12, 1999, the disclosure of which is incorporated herein by reference and with respect to which the present disclosure is a continuation-in-part.

BACKGROUND OF THE INVENTION

Because of their exquisite specificity, biological molecules, including antibodies, have been employed in biosensors. Biosensors are devices capable of identifying and quantifying a target chemical. Biosensors are highly sensitive to their analyte (the chemical species to be detected for an antibody-based biosensor, the analyte is the antigen to the antibody). They are able to detect quantities as small as $10^{-15}$ gram. They are also extremely specific toward the analyte because of the unique ability of the antibodies to recognize their target species at the molecular level.

The present state of the art in antibody-based biosensors is illustrated by the various commercially available immunoassays. An immunoassay is a chemical test based on the use of antibodies to bind the molecule to be detected. In these assays, an antibody specific to the analyte (the "capture antibody") is immobilized onto a solid surface. This surface is then exposed to the sample to be analyzed and the immobilized antibodies bind some of the analyte present in the sample. After the surface is washed, it is immersed in a solution of a second antibody (the "signal antibody") specific to the same analyte. The signal antibody is conjugated (attached chemically) to a radioactive, fluorescent, or enzymatic label, so that it can be detected with high sensitivity. The amount of the signal antibody bound to the analyte is determined by the amount of radioactivity, intensity of fluorescence, or quantity of enzymatic reaction product, which in turn is proportional to the quantity of antigen in the sample. In the case of the enzyme label, the enzyme converts molecules of an added colorless reactant to colored reaction products. The intensity of the color change is read by a spectrophotometer. This type of assay is called enzyme-linked immunosorbent assay (ELISA). Examples of commercially available ELISA test kits are home pregnancy tests and environmental monitoring tests for BTEX (benzene, toluene, ethylbenzene, and xylene), PAH's (polynuclear aromatic hydrocarbons) or PCB's (polychlorinated biphenyls) in water. ELISA assays are also used in the military for battlefield detection of chemical and biological warfare agents. A disadvantage of these immunoassay kits is that a separate kit is required for each antigen or closely related family of antigens being tested for. Not only is this costly and labor consuming when many antigens must be tested for, but it can also result in dangerous time delays as when chemical and biological warfare agents are being tested for on the battlefield.

It would be desirable to provide a single device that could perform multiple immunoassay tests at the same time. The test results of such a device would be read and evaluated automatically. In order to achieve this, each type of antibody must be precisely and discretely located on the test surface. Cross contamination of the antibodies must be avoided. Moreover, such devices should be inexpensive and easy to manufacture.

SUMMARY OF THE INVENTION

Accordingly, an object of this invention is to provide a new device using multiple antibodies on a substrate to perform multiple immunoassay tests.

Another object of this invention is to provide a new device using multiple antibodies on a substrate to perform multiple immunoassay tests whose results can be read automatically.

A further object of this invention is to provide a new, inexpensive method of producing a device using multiple antibodies to perform multiple immunoassay tests.

Yet another object of this invention is to provide a new method of patterning multiple antibody types in discrete groups in precise locations.

These and other objects of this invention are achieved by providing a serial process for producing a multiple antibody patterned substrate by (1) coating an antibody-adsorbent substrate with an antibody-resistant material, (2) removing a portion of the antibody-resistant material by mechanical scribing to produce a bare site on the antibody-adsorbent substrate having a precise size, shape, and location on the substrate, (3) adsorbing molecules of a selected antibody on to the bare site on the antibody-adsorbent substrate, (4) rinsing the substrate to remove unadsorbed antibody molecules, (5) coating the antibody-adsorbent substrate with more of the antibody-resistant material to cover the bare surface of the substrate between the newly adsorbed antibody molecules, and (6) repeating steps (2) through (5) until each of the antibodies has been adsorbed at its specific site on the antibody-adsorbent substrate.

Alternatively, the multiple antibody patterned substrate is produced by a parallel process of (1) coating an antibody-adsorbent substrate with an antibody-resistant material that is resistant to the adsorption of antibodies, (2) simultaneously removing portions of the antibody-resistant material by mechanical scribing to produce bare sites on the antibody-adsorbent substrate having precise sizes and shapes and each site having a precise location which corresponds to a specific antibody, (3) adsorbing molecules of each antibody to its specific bare site on the antibody-adsorbent substrate, (4) rinsing the substrate to remove unadsorbed antibodies, and (5) coating the antibody-adsorbent substrate with more of the antibody-resistant material to cover the bare surface of the substrate between the adsorbed antibody molecules.

Another aspect of this invention is a biosensing device having (A) an analyte-capturing structure comprising (1) an antibody-adsorbent substrate, (2) two or more antibodies adsorbed to the substrate, wherein each antibody is located at a specific site on the substrate apart from the other antibodies, and (3) an antibody-resistant material covering the substrate between the adsorbed molecules of the antibodies for immobilization thereof at discrete locations, and (B) means for determining the types and quantities of the analytes captured by the antibodies.

BRIEF DESCRIPTION OF DRAWING

A more complete appreciation of the invention and many of its attendant advantages will be readily appreciated as the same becomes better understood by reference to the following detailed description when considered in connection with the accompanying drawing wherein.

DETAILED DESCRIPTION OF PREFERRED EMBODIMENTS

Figure 1:
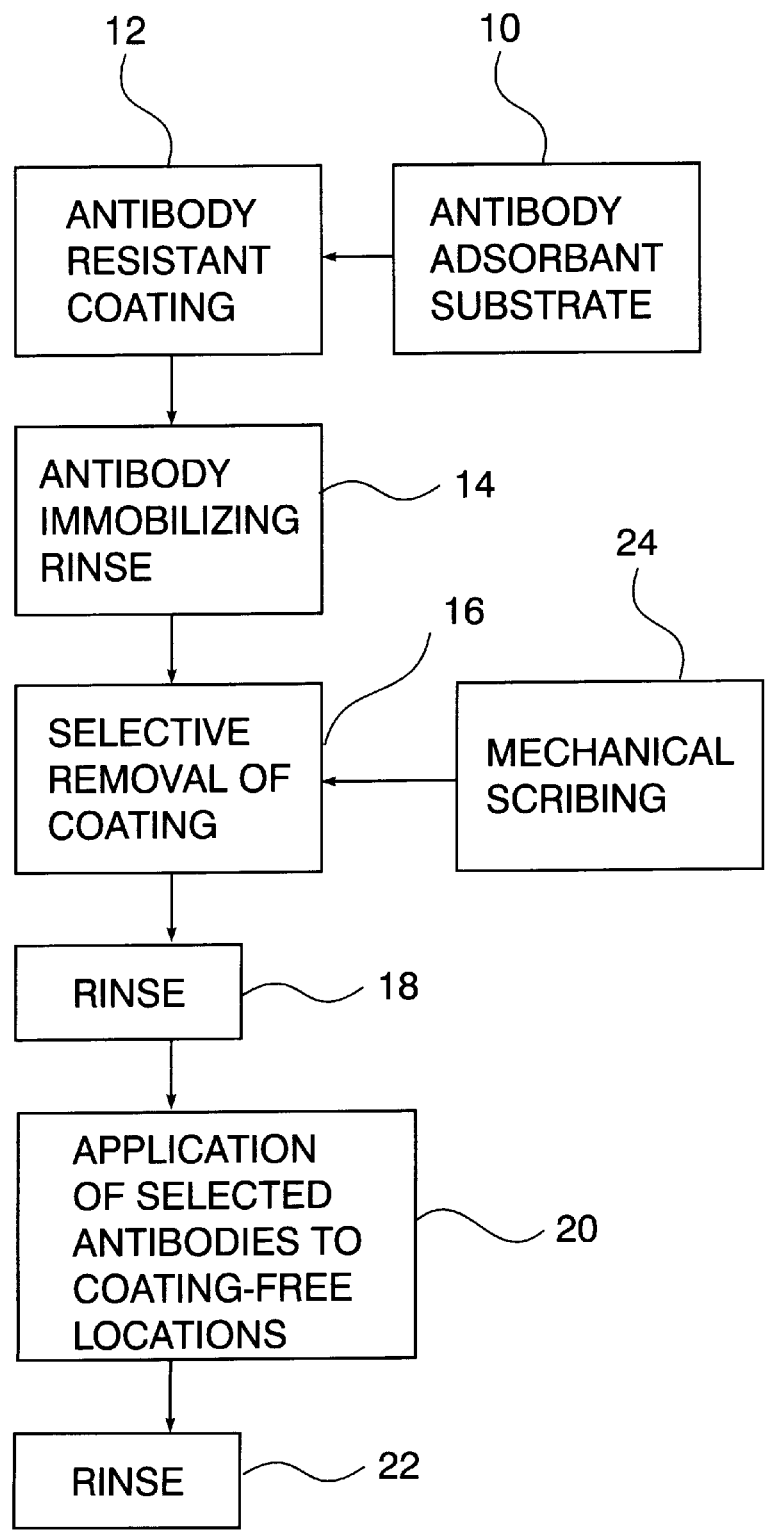
FIG. 1 is a block diagram of an antibody patterning fabrication process, in accordance with an economical embodiment of the present invention.

The present invention provides methods of producing biosensor substrates or chips having multiple antibodies patterned on them. Each antibody is present on the substrate in a specific amount and at a specific location. As a result the output of the substrate can be read automatically to identify and quantify the antigens or analytes present in a sample. The antibodies are separated from each other by an antibody-resistant coating on the substrate which reduces the danger of cross-reactivity between antibody sites and of nonspecific adsorption of antigen. Finally, the methods provide means of patterning many antibodies on a single substrate. This provides the device with the ability to detect multiple chemical species (analytes) or to detect a single species with multiple binding affinities, giving the device a wide range of response and reset times.

The multiple-antibody patterned substrate may be prepared by using either a serial process (as in the examples) or a parallel process. In the serial process, an antibody-adsorbent substrate is coated with an antibody-resistant material. The substrate is then placed in vacuum and an ion beam is used to sputter (etch) away the antibody-resistant coating to expose the surface of the antibody-adsorptive substrate at a selected area. Alternatively, a laser beam could be used to burn or ablate away the antibody-resistant coating to expose the surface. In still another variation, the antibody-resistant material could be precisely removed by mechanical scribing using atomic force microscopy. The substrate is then incubated in a first antibody which results in a large concentration of the first antibody adsorbing on the exposed surface of the antibody-adsorptive material and very little antibody adsorbing on the antibody-resistant coating. The substrate is then rinsed to remove any unadsorbed antibody while leaving the antibody adsorbed to the antibody-adsorbing substrate. Next the substrate is again coated with the antibody-resistant coating. This is a conventional procedure called blocking the surface and it results in any bare surface between the adsorbed antibody molecules being covered with antibody-resistant material. When the other antibodies are applied later they will not be able to attach to this area of the antibody-adsorbent substrate and contaminate it; also antigens will not be able to attach to this area of the substrate. The procedure is then repeated at a new site with a new antibody and this is continued until all the desired antibodies are on the substrate. A final antibody-resistant coating is applied to block the surface around the last antibody adsorbed.

Ion beam sputtering (etching) is used to remove the antibody-resistant coating and expose precise areas of antibody-adsorbent substrate at precise locations. This feature is critical to the production of automated biosensors. The shaping and positioning of the exposed areas may be achieved by using masks or by using a programmable ion beam sputtering device. A high spatial resolution of ion beams permits large numbers of antibody locations to be produced on the substrate. In an alternative embodiment, a laser beam is used to burn or ablate off the antibody-resistant coating in place of ion beam sputtering. Precise shaping and positioning of the exposed areas can be achieve by using masks with the laser or by using a programmable laser. Mechanical scribing using atomic force microscopy provides yet another method of precisely shaping and positioning the exposed areas.

On an industrial scale, it may be preferable to use a parallel process to produce the multiple antibody patterns on the substrates. An ion beam sputtering machine with masks or a programmable ion beam sputtering machine would be used to etch a large number of bare spots on the antibody-adsorbent substrate at once. Alternatively, a laser with a mask or a programmable laser could be used to ablate or burn off the antibody-resistant material from the antibody-adsorbent substrate at a large number of spots at one time. Such removal of anti-body resistant material could also be achieved by mechanical scribing using atomic force microscopy. In the next step, an array of micropipets could be used to deliver each antibody to the correct bare spot (site) and none other. The coating of antibody-resistant coating which separates the etched areas from each other is critical in this process to prevent the cross contamination of antibodies, or adsorption of the antigen in unwanted areas. Ink jet printing technology might be used in place of the micropipets. A final antibody-resistant coating is then applied to block or cover the bare substrate surface around each of the adsorbed antibody molecules. This step is necessary to prevent antibody contamination of the substrate during storage or use of the device, or to allow a false positive reading due to nonspecific antigen adsorption.

The antibody-adsorbent substrate may be composed of any material conventionally used to physically adsorb proteins or antibodies. The adsorption should be a spontaneous, physical process. In general, any hydrophobic material should be suitable for this purpose. Polystyrene and polypropylene are the two most commonly used. However, many other hydrophobic polymeric materials such as polyethylene or copolymers of polyethylene and polypropylene will also work well. The use of cross-linking agents or other chemical agents to chemically bind the antibodies to the substrate are excluded from the processes of this invention.

The antibody-resistant coating is composed of a material which is resistant to antibody (protein) adsorption and which can be etched away in high yield and resolution by using ion beam sputtering or be ablated away by a laser beam, or be removed by mechanical scribing. Examples of preferred antibody-resistant coatings include (1) bovine serum albumin, (2) gelatin, (3) lysozyme, (4) octoxynol, (5) polysorbate 20, and (6) polyethylene oxide-containing block copolymer surfactants. Octoxynol can be represented by the formula

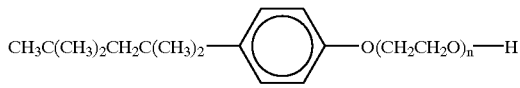

Wherein n is preferably from 9 to 10. The antibody-resistant polyethylene oxide-containing block copolymer surfactants include those containing polyethylene oxide-polypropylene oxide copolymer blocks and those containing polyethylene oxide-polybutylene oxide copolymer block. These surfactants are discussed by Jin Ho Lee et al. In "Protein-resistant surfaces prepared by PEO-containing block copolymer surfactants", *Journal of Biomedical Materials Research*, Vol. 23, pp. 351–368 (1989), herein incorporated by reference in its entirety. The more preferred antibody-resistant coatings are bovine serum albumin, gelatin, and lysozyme, with bovine serum albumin being the most preferred.

The multiple antibody patterned substrates of this invention function as multiple analyte or antigen capturing structures that are suitable for automatic analysis. Each analyte is identified by the position (site) of the antibody that captures it on the substrate. Conventional radioactive, fluorescent, or enzymatic labels can be used to mark the captured analytes for detection and measurement. The amount of radioactivity, intensity of fluorescence, or quantity of enzymatic reaction product (color change) is proportional to the quantity of the specific analyte captured by the specific antibody at the specific site. The quantity of analyte capture will be proportional to the concentration of the analyte present in the test environment (solution, air, blood, water, etc.) and the quantity of the capturing antibody present on the substrate at that site. The quantity of the antibody is controlled by the conditions under which the antibody was originally adsorbed on the antibody-adsorbent substrate and by the area of bare substrate available for antibody adsorption. The intensity of the label signals from the various sites on the substrate provides a complete picture of the concentrations of the analytes found in the test environment.

In regard to the foregoing description, various examples are presented as specific embodiments in U.S. Pat. No. 5,858,801 aforementioned. Pursuant to the disclosure hereinafter set forth, an embodiment for patterning many antibodies in parallel by selective removal of antibody resistant coating material from discrete locations on the surface of an antibody adsorbent substrate, is presented. Such coating removal step is performed in such a manner as to achieve a drastic reduction in fabrication time by limitation to mechanical or physical patterning of plural antibodies in parallel on a substrate.

As diagrammed in FIG. 1, an antibody adsorbent substrate 10 initially undergoes a surface coating step 12. The substrate according to one embodiment is made of polystyrene and has an approximate dimension of 10×5 mm. Such substrate 10 undergoes coating 12 with an antibody resistant material such as bovine serum albumin (BSA) by immersion of the substrate in a 1% w/v solution of the BSA at room temperature for approximately 30 minutes, followed by step 14 for antibody immobilization by rinse in an antigen such as phosphate buffered saline (PBS) for 2 hours under a temperature of 37° C. The BSA coating was then selectively removed from discrete locations on the substrate surface in accordance with coating removal step 16, followed by another PBS rinse step 18 before application of selected antibodies in parallel to coating free locations on the substrate in accordance with step 20. The process is completed by a contamination preventing rinse in deonized water as step 22. An important aspect of the foregoing diagrammed process resides in the coating removal step 16, which is physical or mechanical in nature as a result of the use of a macro-stylus for mechanical scribing 24 as denoted in FIG. 1, which does not involve any chemical or biological activity as in the case of ion beam sputtering, to not only reduce material costs but to also reduce processing time. While sputtering type of coating removal step disclosed in U.S. Pat. No. 5,858,801 produced a clean enough polystyrene substrate surface for antibody adsorption, it was found that use of mechanical scribing for coating removal pursuant to the present invention is also capable of providing a sufficiently clean polystyrene substrate surface for antibody adsorption.

Antibody patterning using a stainless steel scribe was demonstrated by use in the preparation of two samples, as a much faster approach than ion beam sputtering for removal of BSA from a polystyrene surface. Such mechanical scribing took just a few seconds for each area scribed as part of a procedure otherwise similar to that for patterning with ion beam sputtering. The BSA was selectively removed along an approximately 100 μm wide line by scribing the sample surface with the stainless steel scribe (Techni-Tool, Plymouth Meeting, Pa.) using a pressure of approximately $2×10^7$ Pa, followed by a rinse in PBS. The precise value of the pressure is not expected to be critical, provided it is above the threshold for displacing BSA. The sample was then immersed in a solution of the R-α-G antibody. The antibody binds to the clean polystyrene surface exposed by the scribe, but not to the BSA-coated polystyrene. The sample was then rinsed in PBS, blocked by immersing in BSA solution for 30 minutes at room temperature, and rinsed in PBS. Then, the sample surface was scribed again, along a line intersecting and approximately perpendicular to the first line. Following a PBS rinse, the sample was immersed in a solution of R-α-C, the antibody that does not bind the fluorescently labeled antigen. This was followed by a PBS rinse, a BSA block and a PBS rinse. Finally, the sample was immersed in a solution of the fluorescently labeled antigen, G-α-M/FITC. To rule out nonspecific adsorption of antibody or antigen on undesired areas of the surface, and demonstrate functionality of the first antibody, one of the two samples was fabricated by reversing the order of antibody immobilization.

Figure 2:
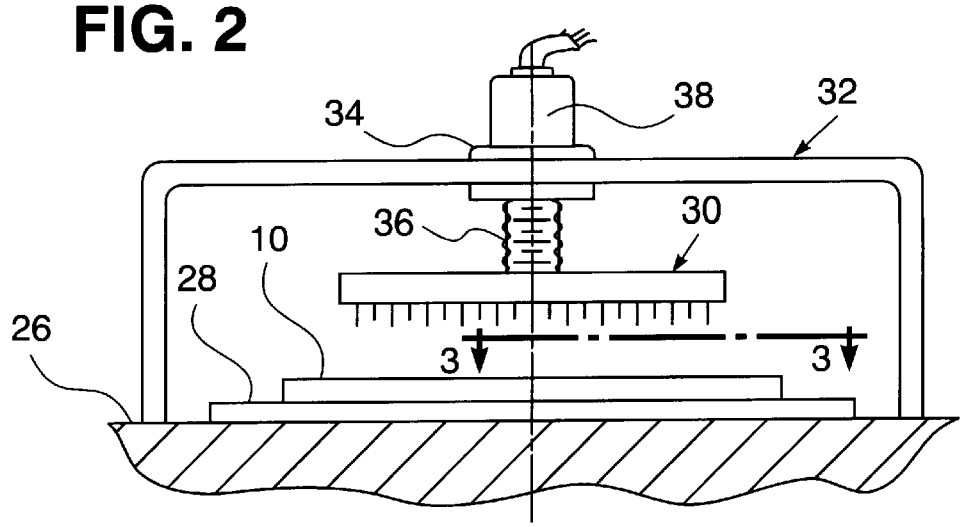
FIG. 2 is a side view of apparatus for mechanical removal of coating from the surface of a substrate, associated with the patterning fabrication process diagrammed in FIG. 1.
Figure 3:
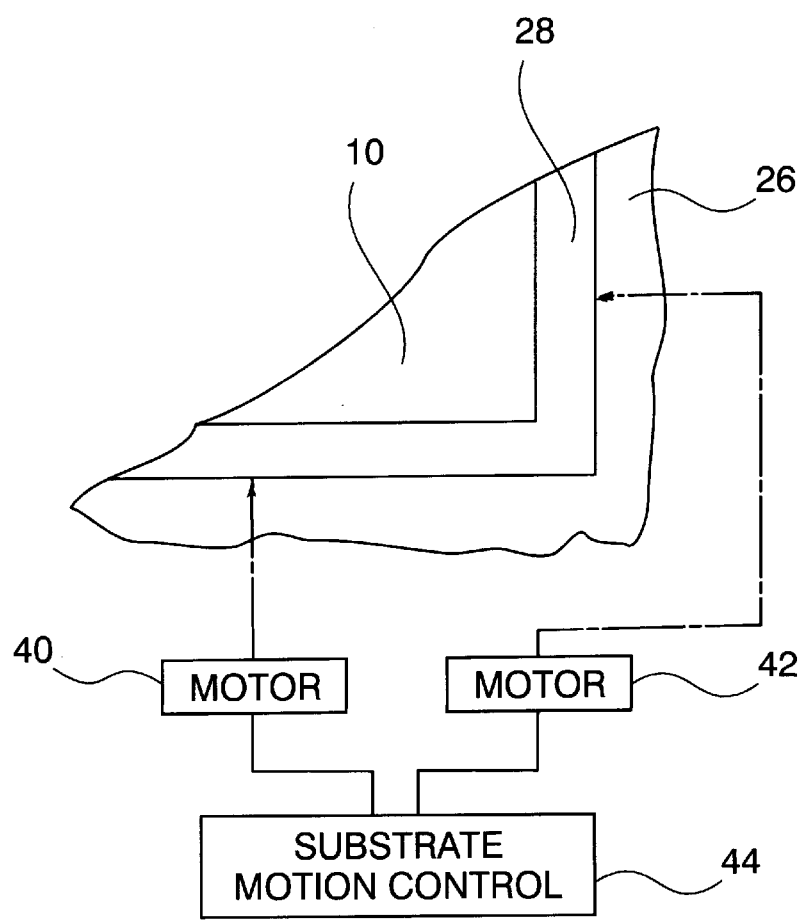
FIG. 3 is a partial top plan view observed from section line 3—3 in FIG. 2, with schematically diagrammed apparatus components associated therewith.

FIGS. 2 and 3 schematically illustrate an example of mechanical scribing 24, simultaneously applied to many positions on a surface associated with the selective coating removal step 16 denoted in FIG. 1. Such coating removal may be performed for example on the surface of a base 26 supporting a flat, horizontally movable platform 28 onto which the polystyrene substrate 10 to be patterned is adjustably positioned underlying a stylus array 30 of pixels for simultaneous removal of antibody resistant coating from discrete locations on the substrate 10. The stylus array 30 is supported by means of some frame structure 32 attached to the base 26 having an internally threaded nut 34 through which a finely threaded screw 36 extends. Such screw 36 is attached at its lower end to the stylus array 30 and is rotatably driven by motor 38 for lowering the array of pixels into scribing contact with the substrate 10 under appropriate force for removal of the BSA coating in response to lateral movement of the substrate 10 in two perpendicular intersecting directions imparted to the substrate through supporting platform 28. As denoted by way of example in FIG. 3, schematically diagrammed precision motors 40 and 42 impart such movement to the platform 28 under substrate motion control 44 causing the stylus pixels of array 30 to effectively remove the coating from discrete locations on the substrate 10 for subsequent antibody adsorption.

The foregoing described mechanical scribing type of coating removal is most effective in conjunction with the parallel antibody immobilization rinsing approach to antibody patterning, so as to provide for inexpensive fabrication of single-use substrates in conjunction with charge-coupled detectors.

Obviously, other modifications and variations of the present invention may be possible in light of the foregoing teachings. It is therefore to be understood that within the scope of the appended claims the invention may be practiced otherwise than as specifically described.

What is claimed is:

1. In a method of patterning antibodies on a substrate to which a coating resistant to antibody absorption is applied and from which removal of the coating is effected at discrete locations thereon to expose antibody absorbent surfaces onto which the antibodies are applied, the improvement comprising: limiting said removal of the coating to a step of physical displacement thereof from said surfaces on the substrate at said discrete locations thereon to reduce costs and minimize processing time.

2. The method as defined in claim 1, wherein said removal of the coating from the discrete locations is performed by movement of a stylus into physical contact with said substrate.

3. The method as defined in claim 2, wherein said step of physical displacement of the coating includes: selectively imparting movement to the substrate in intersecting directions parallel to said exposed surfaces thereof during said physical contact with the stylus.

4. In a method of patterning antibodies on a substrate from which a coating resistant to antibody absorption is removed at discrete locations thereon exposing antibody absorbent surfaces onto which the antibodies are applied, the improvement comprising the step of: mechanical displacement of the coating for removal from said discrete locations by physical scribing contact of a stylus with said surfaces on the substrate.

5. In a method of patterning antibodies on a substrate from which a coating resistant to antibody absorption is removed at discrete locations thereon exposing antibody absorbent surfaces onto which the antibodies are applied, the improvement comprising the steps of: mechanical displacement of the coating for removal from said discrete locations by physical scribing contact of a stylus with said surfaces on the substrate; and controlling said physical scribing contact by the stylus to effect said removal of the coating from the discrete locations by motion selectively imparted to the substrate in intersecting directions parallel to said surfaces thereon.

\* \* \* \* \*